(12) United States Patent
Elomari et al.

(10) Patent No.: US 7,727,925 B2
(45) Date of Patent: *Jun. 1, 2010

(54) REGENERATION OF IONIC LIQUID CATALYST BY HYDROGENATION USING METAL AND ACID

(75) Inventors: Saleh Elomari, Fairfield, CA (US); Thomas V. Harris, Benicia, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 859 days.

This patent is subject to a terminal disclaimer.

(21) Appl. No.: 11/316,629

(22) Filed: Dec. 20, 2005

(65) Prior Publication Data
US 2007/0142217 A1    Jun. 21, 2007

(51) Int. Cl.
| | |
|---|---|
| B01J 20/34 | (2006.01) |
| B01J 21/20 | (2006.01) |
| B01J 23/90 | (2006.01) |
| B01J 25/04 | (2006.01) |
| B01J 27/28 | (2006.01) |
| B01J 29/90 | (2006.01) |
| B01J 38/48 | (2006.01) |
| B01J 38/60 | (2006.01) |
| B01J 31/00 | (2006.01) |
| B01J 31/40 | (2006.01) |
| B01J 38/00 | (2006.01) |

(52) U.S. Cl. .................. 502/150; 502/20; 502/22; 502/27

(58) Field of Classification Search ........ 502/150, 502/20, 22, 27
See application file for complete search history.

(56) References Cited

U.S. PATENT DOCUMENTS

| | | | |
|---|---|---|---|
| 4,122,245 | A | 10/1978 | Nardi et al. |
| 4,463,071 | A | 7/1984 | Gifford et al. |
| 4,463,072 | A | 7/1984 | Gifford et al. |
| 5,104,840 | A | 4/1992 | Chauvin et al. |
| 5,731,101 | A | 3/1998 | Sherif et al. |
| 6,096,680 | A | 8/2000 | Park |
| 6,797,853 | B2 | 9/2004 | Houzvicka et al. |
| 2004/0077914 | A1 | 4/2004 | Zavilla et al. |
| 2004/0133056 | A1 | 7/2004 | Liu et al. |

OTHER PUBLICATIONS

Adams et al., Chem. Commun., entitled "Stereoselective hydrogenation . . . aromatic compounds", 1999, 1043-1044.*
Adams et al., Chem. Commun., 1998, 2097-2098.*
Wilkes et al., Inorg. Chem., 1982, 21, 1263-1264.*
Christopher J. Adams, et al., Stereoslective hydogenation reacations in chloroaluminate (III) ionic liquids: a new method for the reduction of aromatic compounds, Institute of Applied Catalysis, Schoold of Chemistry, 1999, 1043-1044, Received in Cambridge, UK) 15th Feb. 1999, Accepted 19th Apr. 1999.
Adams, Chistopher J. et al., Friedel-Crafts reactions in room temperature ionic liquids, 1998. 2097.2098, Chem. Commun.

* cited by examiner

*Primary Examiner*—Jerry Lorengo
*Assistant Examiner*—James E McDonough
(74) *Attorney, Agent, or Firm*—Susan M. Abernathy; Steven H. Roth

(57) ABSTRACT

A process for regenerating a used acidic ionic liquid catalyst which has been deactivated by conjunct polymers comprising combining the used catalyst, a metal and a Broensted acid which acts a source of hydrogen in a reaction zone under hydrogenation conditions for a time sufficient to hydrogenate at least a portion of the conjunct polymer is disclosed.

25 Claims, 1 Drawing Sheet

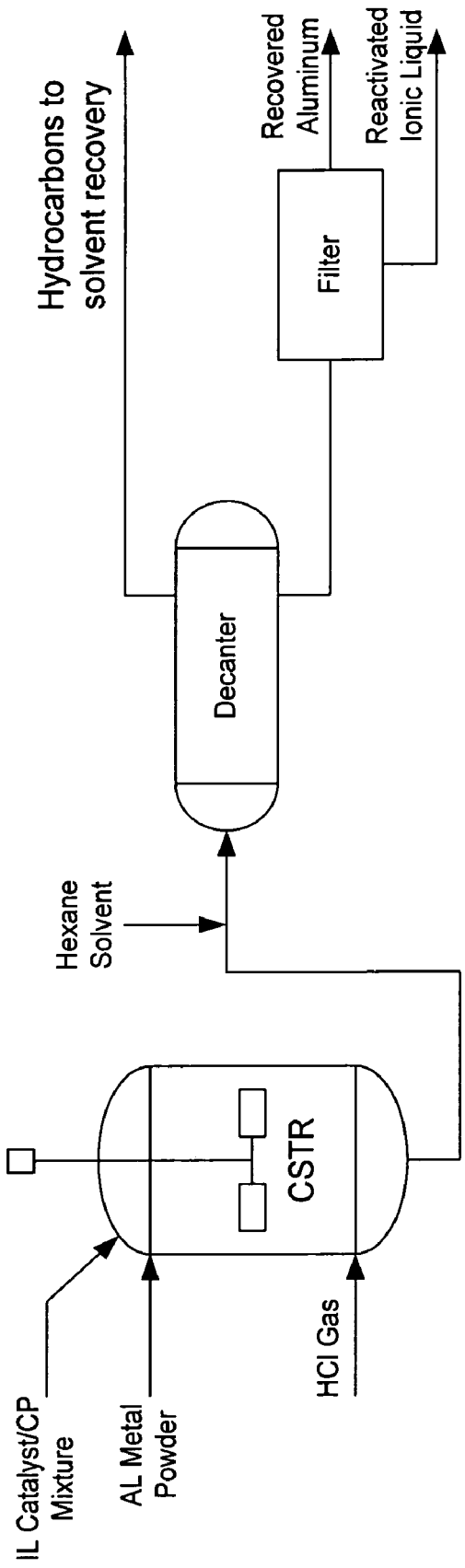

ns. Friedel-Craft reactions are reactions which fall within the broader category of electrophylic substitution reactions including alkylations.

Other examples of ionic liquids and their methods of preparation may also be found in U.S. Pat. Nos. 5,731,101; 6,797,853 and in U.S. Patent Application Publications 2004/0077914 and 2004/0133056.

Hydrogenation in chloroaluminate ionic liquids in the presence of an electropositive metal and HCl was reported by K. R. Seddon et al in *Chem. Commun.*, 1999, 1043-1044.

As a result of use, ionic liquid catalysts become deactivated, i.e. lose activity, and may eventually need to be replaced. However, ionic liquid catalysts are expensive and replacement adds significantly to operating expenses by in some cases requiring shut down of an industrial process. One of the heretofore unsolved problems impeding the commercial use of chloroaluminate ionic liquid catalysts has been the inability to regenerate and recycle them. The present invention provides methods to regenerate acidic chloroaluminate ionic liquid catalysts overcoming this obstacle and paving the way for the practical, commercial use of these environmentally friendly catalysts.

REGENERATION OF IONIC LIQUID CATALYST BY HYDROGENATION USING METAL AND ACID

FIELD OF THE INVENTION

The present invention relates to methods for the regeneration of catalysts and more specifically to the regeneration of ionic liquid catalysts.

BACKGROUND OF THE INVENTION

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids are those derived from ammonium halides and Lewis acids (such as $AlCl_3$, $TiCl_4$, $SnCl_4$, $FeCl_3$ . . . etc). Chloroaluminate ionic liquids are perhaps the most commonly used ionic liquid catalyst systems.

Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 to describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Aluminum-containing catalysts are among the most common Lewis acid catalysts employed in Friedel-Craft reac-

SUMMARY OF THE INVENTION

The present invention provides, among other things, a process for regenerating a used acidic ionic liquid catalyst comprising combining the used catalyst, a metal and a Broensted acid which acts as a source of hydrogen in a reaction zone under hydrogenation conditions for a time sufficient to increase the activity of the ionic liquid catalyst.

In one embodiment, the present invention provides a process for regenerating a used acidic ionic liquid catalyst which has been deactivated by conjunct polymers comprising the steps of combining the used ionic liquid catalyst, a metal and HCl in a reaction zone under hydrogenation conditions for a time sufficient to hydrogenate at least a portion of the conjunct polymer; removing reaction product from the reaction zone; mixing the removed reaction product with a hydrocarbon solvent in which the hydrogenated conjunct polymers are soluble; allowing the mixture to separate into two phases, a lighter phase which contains the hydrogenated conjunct polymers and a denser phase which contains a regenerated ionic liquid catalyst; and recovering at least a portion of the heavier phase.

BRIEF DESCRIPTION OF THE DRAWING

The FIGURE is a process diagram of an embodiment of a process in accordance with the invention.

DETAILED DESCRIPTION

The present invention relates to a process for the regeneration of spent or deactivated acidic ionic liquid-based catalysts i.e. those catalysts which have lost all or some of their catalytic activity. The present process is being described and exemplified with reference certain specific ionic liquid catalysts and processes catalyzed thereby, but such description is not intended to limit the scope of the invention. The methods described may be applied to other catalysts and processes by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is al-alkyl-pyridinium chloroaluminate, such as 1-butyl-pyridinium heptachloroaluminate.

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid in a combination with a small concentration of a Broensted acid, is a preferred catalyst component in the ionic liquid catalyst scheme.

While not being bound to this or any other theory of operation, the present invention is based in part on our discovery that one of the major catalyst deactivation mechanisms is the formation of by-products known as conjunct polymers. The term conjunct polymer was first used by Pines and Ipatieff to distinguish these polymeric molecules from the usual polymers. Unlike typical polymers, conjunct polymers are polyunsaturated cyclic, polycyclic and acyclic molecules formed by concurrent acid-catalyzed reactions including, among others, polymerization, alkylation, cyclization, and hydride transfer reactions. Conjunct polymers consist of unsaturated intricate network of molecules that may include one or a combination of 4-, 5-, 6- and 7-membered rings in their skeletons. Some examples of the likely polymeric species were reported by Miron et al. (*Journal of chemical and Engineering Data*, 1963) and Pines (*Chem. Tech*, 1982). These molecules contain double and conjugated double bonds in intricate structures containing a combination of cyclic and acyclic skeletons.

The conjunct polymers deactivate the chloroaluminate ionic liquid catalysts by weakening the acid strength of the catalyst through the formation of complexes of conjunct polymers and $AlCl_3$ possibly by means of electron-donor/electron-acceptor interactions. The conjunct polymers with their double bonds are the donors and the Lewis acid ($AlCl_3$) is the acceptor. Using their double bonds, the conjunct polymers coordinate to the Lewis acid ($AlCl_3$) in the ionic liquid and rendering the coordinated $AlCl_3$ for catalysis. Thus, the acidity of the catalyst becomes weaker and the overall catalytic activity becomes compromised and no longer effective for the intended purpose. Thus, the catalyst performance will become a function of the concentration of conjunct polymers in the ionic liquid phase. As more conjunct polymers accumulate in the ionic liquid phase the catalyst becomes less active. So, removal of all or a suitable portion of the conjunct polymers from the ionic liquid phase is a significant aspect of the present process for ionic liquids catalyst regeneration.

The term "conjunct polymer" as used herein also includes any other species which might complex to $AlCl_3$ by pi bonding or sigma bonding or other means, which results in those species binding to the ionic liquid, so they are not removable by simple hydrocarbon extraction.

It is believed that deactivation of the catalyst by the presence of conjunct polymers is, in part at least, caused by coordination and complex formation between the Lewis acid $AlCl_3$ (electron pair acceptor) and the conjunct polymers (electron donors). In such complexes, the $AlCl_3$ is no longer available to act as a catalyst since it is tied-up in the $AlCl_3$-conjunct polymers complexes. It also appears that the presence (or accumulation) of conjunct polymer molecules in the catalyst phase is not by virtue of being miscible in the ionic liquid phase. While conjunct polymers may be somewhat miscible in the ionic liquids, their accumulation in the catalyst phase is more likely to being bound by strong acid-base interactions (complexation) rather than being soluble in the ionic liquid phase.

Conjunct polymers isolated from the catalyst phase by means of hydrolysis are highly soluble in hydrocarbons. However, attempts to remove them from the catalyst phase prior to hydrolysis by simple extraction methods with hydrocarbon solvents such as hexane, decane and toluene were unsuccessful. Other more polar solvents such as $CH_2Cl_2$ or chloroform may dissolve a chloroaluminate ionic liquid and therefore are not a selective solvent for dissolving and removing the conjunct polymers. Conjunct polymers may be isolated by hydrolysis. However, these methods of isolating the conjunct polymers are destructive, and result in an actual loss of a catalytic component ($AlCl_3$). The hydrolysis methods hydrolyze the catalytic component ($AlCl_3$) and transform it into inactive aluminum hydroxide and aluminum oxide. This indicates that the conjunct polymers are tightly held in the ionic liquid phase by fairly strong type of bonding system. Therefore, any successful attempt to reactivate and regenerate the catalyst must involve the removal of conjunct polymers to release aluminum trichloride from the $AlCl_3$-conjunct polymer complexes without destroying, consuming, or irreversibly tying up the $AlCl_3$.

In other words, one objective is to free the catalyst by replacing the conjunct polymers with other basic species that simply displace the polymer without destroying the catalyst or by suppressing the ability of conjunct polymers to form complexes with Lewis acids (aluminum chloride).

The deactivated catalyst can be revived in a nondestructive manner by freeing up the $AlCl_3$ from conjunct polymer-$AlCl_3$ complex. In principle, this can be accomplished by saturation of the double bonds of the conjunct polymers to eliminate their ability to coordinate to the Lewis acid ($AlCl_3$). By hydrogenation, the double bonds of the conjunct polymers will be saturated and no longer be able to be coordinated or complexed to $AlCl_3$. $AlCl_3$ no longer bound by conjunct polymers is then released to take part in catalytic reactions.

Aluminum metal reacts with HCl to give hydrogen gas and $AlCl_3$. By introducing aluminum metal and HCl into ionic liquid catalysts deactivated by conjunct polymers, the hydrogen liberated can be used to saturate the conjunct polymer double bonds. Concurrently, fresh aluminum chloride is produced, which is the acid component in the chloroaluminate ionic liquid. This constitutes a two-function regeneration scheme for both hydrogenating the conjunct polymers to release the complexed $AlCl_3$ and producing fresh $AlCl_3$ which replenishes $AlCl_3$ that has been consumed or lost by other means during the reaction. The hydrogenated conjunct polymers can be removed by solvent extraction or decantation and the regenerated ionic liquid catalyst recovered by filtration. Our experiments have shown that this scheme is feasible and that the regenerated catalyst demonstrated equal or better activity for the alkylation of ethylene with isopentane compared with freshly prepared catalyst.

Among other things, the present invention provides a process to maintain an acceptable level of ionic liquid catalyst activity in an alkylate production process by reactivating or regenerating the catalyst using aluminum metal combined with HCl injection to release $AlCl_3$ from conjunct polymers and concurrently produce fresh AlCl$_3$. The reactivation process may be employed continuously or batch-wise on a whole or partial slipstream of the catalyst recycled from the alkylation reactor.

An embodiment of a process according to the present invention utilizes hydrogenation to saturate the double bonds of conjunct polymers using aluminum metal and hydrochloric acid. Using aluminum metal and HCl will produce the needed hydrogen gas for the hydrogenation and will also produce fresh AlCl$_3$ that increases the acidity and the activity of the recycled catalyst by increasing the concentration of AlCl$_3$ in the ionic liquid to its upper limits. In some cases, the regenerated catalyst will be more active than the freshly prepared catalyst prior to being deactivated. The metal used in the regeneration process in accordance with the present invention is not limited to aluminum. Other electropositive metals will react with HCl to produce H$_2$ and the corresponding metal chloride can also be used. This includes sodium, lithium, zinc, iron, copper, magnesium, titanium, gallium and many others. Aluminum metal will be the metal of choice when chloroaluminate ionic liquids are used in the catalytic process to avoid contamination of the regenerated ionic liquid with metal chlorides other than AlCl$_3$. While some metal chlorides may work as co-catalyst, others may inhibit the alkylation mechanism and promote unwanted reaction pathway. The process is not limited to using HCl as the source of hydrogen. Other Broensted acids may also be used as a source of hydrogen including, but not limited to, HI, HBr, HF, H$_2$SO4, H$_3$PO$_4$.

In the case of chloroaluminate ionic liquids, hydro halides (HI, HCl, HBr, HF) will be the acids of choice. Among the hydro halides hydrochloric acid is preferred to avoid introduction of conjugate bases other than halides and preferably other than chlorides.

As shown in the Examples which follow, the conjunct polymers are removed by hydrogenation using aluminum and hydrogen chloride. Adding aluminum and hydrogen chloride to used ionic liquid catalyst and stirring the resulting mixture (in autoclave) at room temperature or at 50° C. at the autogenic pressure led to removal of >90% of the conjunct polymers as hydrogenated hydrocarbons. The hydrogenated conjunct polymers (immiscible in the ionic liquid phase) were removed by simple extraction methods with other hydrocarbons (such as hexanes) or by means of decanting. The regenerated ionic liquid catalyst was removed from the remaining mixture (freshly made AlCl$_3$ and aluminum metal) by filtration.

The recovered ionic liquid catalyst (by filtration) was tested for activity by alkylating ethylene with isopentane and the regenerated catalyst showed better activity than both the deactivated catalyst and the fresh catalyst from which the deactivated catalyst was made. The selectivity of the regenerated catalyst was identical to the selectivity of the freshly-made catalyst.

In an alkylate production unit, light (C$_2$-C$_5$) olefins and isoparaffin feeds are contacted in the presence of a catalyst that promotes the alkylation reaction. In one embodiment of a process in accordance with the present invention, this catalyst is a chloroaluminate ionic liquid. The reactor, which may be a stirred tank or other type of contactor (e.g., riser reactor), produces a biphasic mixture of alkylate hydrocarbons, unreacted isoparaffins, and ionic liquid catalyst containing some conjunct polymers. The catalyst/conjunct polymer phase may be separated from the hydrocarbons by means of a gravity decanter. This catalyst will be partially deactivated by the conjunct polymers binding to AlCl$_3$. The recovered catalyst can be reactivated in a reaction system employing aluminum metal and HCl. The products of this step will be reactivated catalyst and hydrogenated conjunct polymers. These can be separated by solvent washing, decantation, and filtration.

It is not necessary to regenerate the entire charge of catalyst. In some instances only a portion or slipstream of the catalyst charge is regenerated. In those instances only as much ionic liquid catalyst is regenerated as is necessary to maintain a desired level of catalyst activity in the process in which the ionic liquid is used as the catalyst.

In one embodiment of the present invention with reference to the FIGURE, the ionic liquid catalyst/conjunct polymer mixture is introduced continuously into a stirred tank reactor (CSTR), where aluminum metal powder is added by way of a screw-type feeder. The aluminum is kept under inert gas (nitrogen or other) to prevent oxidation. HCl gas is fed in at the desired rate to produce H$_2$ gas and AlCl$_3$. The residence time of the reactor will be selected to allow adequate hydrogenation of the conjunct polymers. The reaction product is withdrawn and mixed with a hydrocarbon solvent (e.g., hexane) in which the hydrogenated conjunct polymers are soluble. The solvent may be a normal hydrocarbon ranging from C$_5$-C$_{15}$; preferably C$_5$-C$_8$. This mixture is then separated in a gravity decanter, from which the dense ionic liquid phase is withdrawn. Unreacted aluminum in the ionic liquid phase is removed by filtration. The reactivated ionic liquid catalyst is returned to the alkylation reactor. The solvent/conjunct polymer mix is separated by distillation to recover the solvent.

Hydrogenation conditions will generally include temperatures of −20° C.-200° C., preferably 50°-150° C., pressures of atmospheric-5000 psig, preferably 50-500 psig, and a contact time of 0.1 minute-24 hours, and preferably from ½-2 hours in a normal hydrocarbon as a solvent.

The following Examples are illustrative of the present invention, but are not intended to limit the invention in any way beyond what is contained in the claims which follow.

EXAMPLES

Example 1

Preparation of Fresh 1-Butylpyridinium Chloroaluminate Ionic Liquid Catalyst A
(Fresh IL A)

1-butyl-pyridinium chloroaluminate is a room temperature ionic liquid prepared by mixing neat 1-butyl-pyridinium chloride (a solid) with neat solid aluminum trichloride in an inert atmosphere. The syntheses of butylpyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The autoclave was sealed and the neat mixture allowed to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, un-reacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shiny solid. $^1$H-NMR and $^{13}$C-NMR were consistent with the desired 1-butyl-pyridinium chloride and no impurities were observed.

1-butylpyridinium chloroaluminate was prepared by slowly mixing dried 1-butylpyridinium chloride and anhydrous aluminum chloride (AlCl₃) according to the following procedure. The 1-butylpyridinium chloride (prepared as described above) was dried under vacuum at 80° C. for 48 hours to get rid of residual water (1-butylpyridinium chloride is hydroscopic and readily absorbs water from exposure to air). Five hundred grams (2.91 mol.) of the dried 1-butylpyridinium chloride were transferred to a 2-Liter beaker in a nitrogen atmosphere in a glove box. Then, 777.4 gm (5.83 mol.) of anhydrous powdered AlCl₃ (99.99% from Aldrich) were added in small portions (while stirring) to control the temperature of the highly exothermic reaction. Once all the AlCl₃ was added, the resulting amber-looking liquid was left to gently stir overnight in the glove box. The liquid was then filtered to remove any un-dissolved AlCl₃. The resulting acidic 1-butyl-pyridinium chloroaluminate was used as the catalyst for the alkylation of isopentane with ethylene.

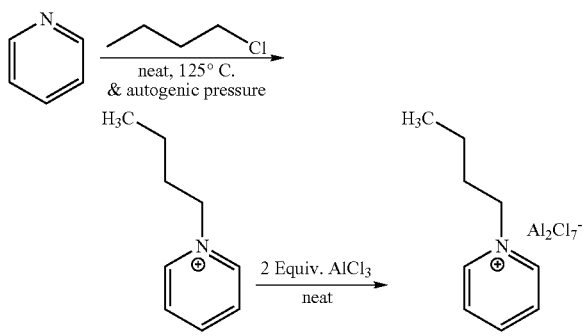

Example 2

Preparation of "Deactivated" 1-Butylpyridinium Chloroaluminate Ionic Liquid Catalyst (Deactivated Catalyst A)

"Deactivated" or "used" 1-butylpyridinium chloroaluminate ionic liquid catalyst was prepared from "fresh" 1-butylpyridinium chloroaluminate ionic liquid catalyst by carrying out the isobutane alkylation reaction in a continuous flow microunit under catalyst recycle with accelerated fouling conditions.

The microunit consists of feed pumps for isobutane and butenes, a stirred autoclave reactor, a back pressure regulator, a three phase separator, and a third pump to recycle the separated ionic liquid catalyst back to the reactor. The reactor was operated at 80 to 100 psig pressure and with cooling to maintain a reaction temperature of ~10° C. To start the reaction, isobutane, butenes, and HCl were pumped into the autoclave at the desired molar ratio (isobutane/butenes>1.0), through the back pressure regulator, and into the three phase separator. At the same time, fresh chloroaluminate ionic liquid catalyst was pumped into the reactor at a rate pre-calculated to give the desired catalyst/feed ratio on a volumetric basis. As the reaction proceeded, ionic liquid separated from the reactor effluent and collected in the bottom of the three phase separator. When a sufficient level of catalyst built up in the bottom of the separator, the flow of fresh ionic liquid was stopped and catalyst recycle from the bottom of the separator was started. In this way, the initial catalyst charge was continually used and recycled in the process.

The following process conditions were used to generate Deactivated Catalyst A (1-butylpyridinium chloroaluminate ionic liquid catalyst) from Fresh Catalyst A:

| Process Variable | |
|---|---|
| Isobutane pump rate | 4.6 g/min |
| Butene pump rate | 2.2 g/min |
| IL Catalyst pump rate | 1.6 g/min |
| HCl flow rate | 3.0 SCCM |
| pressure | 100 psig |
| temperature | 10° C. |

The reaction was continued for 72 hours when it was judged that the catalyst had become sufficiently deactivated.

Example 3

Determination of the Amounts of Conjunct Polymer And Olefin Oligomers In Deactivated IL A The wt % of conjunct polymers in the spent (deactivated) ionic liquid was determined by hydrolysis of known weights of the spent catalyst. The example below is a typical procedure for measuring conjunct polymers in a given spent catalyst. In a glove box, 15 gm of a spent ionic liquid catalyst in a flask were rinsed first with 30-50 ml of anhydrous hexane to remove (from the spent catalyst) any residual hydrocarbon or olefinic oligomers. The hexane rinse was concentrated under reduced pressure to give only 0.02 gm of yellow oil (0.13%). Then, 50 ml of anhydrous hexane was added to the rinsed catalyst followed by slow addition of 15 ml of water, and the mixture was stirred at 0° C. for 15-20 minutes. The resulting mixture was diluted with additional 30 ml hexanes and stirred well for additional 5-10 minutes. The mixture was allowed to settle down to two layers solution and some solid residue. The organic layer was recovered by decanting. The aqueous layer was further washed with additional 50 ml hexanes. The hexanes layers were combined and dried over anhydrous MgSO₄, filtered and concentrated to give 2.5 gm (16.7 wt % of the spent catalyst) of viscous dark orange-reddish oil. It was determined therefore that this particular spent catalyst contains 0.13% oligomers and 16.7% conjunct polymers. The hydrolysis can also be accomplished using acidic (aqueous HCl) or basic (aqueous NaOH) solutions.

Example 4

Characterization of Recovered Conjunct Polymer From Deactivated IL A

The recovered conjunct polymers according to the procedure described in Example 3 were characterized by elemental analysis and by infrared, NMR, GC-Mass and UV and spectroscopy methods. The recovered conjunct polymers have hydrogen/carbon ratio of 1.76 and chlorine content of 0.8%. ¹H-NMR and ¹³C-NMR showed the presence of olefinic protons and olefinic carbons. Infra Red indicated the presence of olefinic regions and the presence of cyclic systems and substituted double bonds. GCMS showed the conjunct polymers to have molecular weights ranging from 150-mid 600s. The recovered conjunct polymers have boiling ranges of 350-1100° F. as indicated by high boiling simulated distillation analysis. UV spectroscopy showed a UV $\lambda_{max}$ at 250 nm pointing highly conjugated double bonds systems.

Example 5

Hydrogenation of Deactivated IL A Using Al Metal And HCl And Determination of the Amount of Residual Conjunct Polymers Saturation of the double bonds of the conjunct polymers using aluminum metal and HCl was achieved according to the procedure shown below. To 40 gm of spent ionic liquid containing 15.5 wt % (6.2 gm) of conjunct polymers in 300 cc autoclave, 100 ml of anhydrous n-hexane and 9 gm of aluminum were added. The autoclave was sealed (all done in glove box), and 10 gm of anhydrous HCl were introduced via an inlet. The reaction was stirred at >1200 rpm and with intent of heating to 75° C. The reaction was very exothermic and after few minutes the temperature rose to 81° C. and the pressure to 290 psi. Then, the pressure and the temperature began to drop. At the end of the run (1.5 hrs) the temperature was at 75° C. and the pressure was at 99 psi. The reactor was cooled to room temperature and the organic phase was decanted off. The ionic liquid phase was rinsed twice with 50 ml anhydrous hexane. The hexane layers were combined and concentrated under reduced pressure and heat to remove the solvent (hexane) giving 5.8 gm (93.5% of the weight of conjunct polymer originally present in the deactivated ionic liquid). Hydrolysis of 10 gm of the treated ionic liquid gave 0.06 gm of conjunct polymers indicating a total of 4% remained in the ionic liquid phase. The hydrogenated products showed normal H/C ratios and NMR, IR and UV spectroscopy all indicated the disappearance of the double bonds.

Example 6

Determination of Activity of Deactivated IL A Using Batch Alkylation of isoPentane With Ethylene The regenerated catalyst was highly active. The activity of the regenerated ionic liquid catalyst matched the activity of the freshly prepared catalyst in the alkylation of ethylene with isopentane to make $C_7$s. Table 1 compares the activity of the regenerated catalyst with the freshly prepared and the spent catalysts in the alkylation of ethylene with isopentane. The alkylation of isopentane with ethylene was done according to the procedure describe below. A 300 cc autoclave was charged with 20 gm of ionic liquid catalyst, 100 gm anhydrous isopentane, 10 gm ethylene and 0.3 gm anhydrous HCl. The reaction was then stirred ~1200 rpm and heated to 50° C. at autogenic pressures. The starting pressure was usually 280-320 psi. The reaction was usually complete when the pressure dropped down to single digits. In the case of slow going reaction, the reaction was allowed to go on for 1 hr. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The following Table 1 draws a comparison among the freshly made, the spent and the regenerated catalysts.

|  | Fresh Catalyst | Spent Catalyst | Regenerated. Catalyst |
|---|---|---|---|
| Reaction Time | 9 min. | 60 min. | 6 min. |
| Starting Pressure | 300 psi | 286 psi | 297 psi |
| Ending pressure | 11 | 302 psi | 7 |
| iC5 | 72 | 98% | 67 |
| C7s | 19 | ~1.4% | 19 |
| 2,3-DM-Pentane | 8.23 | 0.9 | 9 |
| 2,4-DM-Pentane | 10 | 0.6 | 10 |
| 2,3DM/2,4DM | 0.82 | 1.5 | 0.9 |

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for regenerating a used acidic ionic liquid catalyst which has been deactivated by conjunct polymers through use, comprising:
   a. removing the used acidic ionic liquid catalyst from a reaction zone in which said catalyst was used;
   b. combining at least a portion of the used acidic ionic liquid catalyst, a metal and a Broensted acid in a regeneration zone under conditions and for a time sufficient to convert the conjunct polymers into an extractable phase;
   c. removing a reaction product from the regeneration zone;
   d. mixing the removed reaction product with a hydrocarbon solvent in which the conjunct polymers are soluble;
   e. allowing the mixture from step (d) to separate into two phases, a lighter phase which contains the conjunct polymers and a heavier phase which contains a regenerated ionic liquid catalyst; and
   f. recovering at least a portion of the heavier phase that is a regenerated acidic ionic liquid catalyst.

2. A process for regenerating a used acidic ionic liquid catalyst comprising the steps of combining the used acidic ionic liquid catalyst that is a catalyst recycled from an alkylation reactor, a metal and a Broensted acid in a reaction zone under a set of conditions for a time sufficient to increase the activity of the used acidic ionic liquid catalyst; and returning a regenerated acidic ionic liquid catalyst to the alkylation reactor.

3. The process according to claim 1 or claim 2, wherein the metal is selected from the group consisting of sodium, lithium, magnesium, aluminum, titanium, nickel, zinc, copper, iron, gallium, tin and their mixtures.

4. The process according to claim 1 or claim 2, wherein the Broensted acid is selected from the group consisting of HCl, HI, HBr, HF, $H_2SO_4$, $H_3PO_4$ and their mixtures.

5. The process according to claim 1 or claim 2, wherein the metal is aluminum and the Broensted acid is HCl.

6. The process according to claim 1, wherein the used acidic ionic liquid catalyst has been used in the reaction zone to catalyze a Friedel-Craft reaction.

7. The process according to claim 6, wherein the Friedel-Craft reaction is alkylation.

8. The process according to claim 2, wherein the conditions include contacting the used acidic ionic liquid catalyst with sufficient amounts of metal and excess acid to generate sufficient hydrogen gas at temperatures of −20° C.-200° C., pressures of atmospheric-5000 psig, and in a normal hydrocarbon as a solvent.

9. The process according to claim 1 or claim 2, wherein the hydrocarbon solvent is selected from the group consisting of normal hydrocarbons ranging from $C_5$-$C_{15}$.

10. The process according to claim 1, wherein the used acidic ionic liquid catalyst comprises an imidazolium, a pyridinium, a phosphonium, a tetralkylammonium derivative, or their mixtures.

11. The process according to claim 1 or claim 2, wherein the used acidic ionic liquid catalyst is a chloroaluminate ionic liquid.

12. The process according to claim 10, wherein the used acidic ionic liquid catalyst is a chloroaluminate ionic liquid.

13. A process for regenerating a used acidic ionic liquid catalyst, comprising: removing the used acidic ionic liquid catalyst from a reaction zone in which said catalyst was used; combining at least a portion of the used acidic ionic liquid catalyst, a metal and a Broensted acid in a regeneration zone under conditions and for a time sufficient to increase the activity of the used acidic ionic liquid catalyst.

14. The process according to claim 13 wherein the metal is selected from the group consisting of sodium, lithium, magnesium, aluminum, titanium, nickel, zinc, copper, iron, gallium, tin and their mixtures.

15. The process according to claim 13, wherein the Broensted acid is selected from the group consisting of HI, HBr, HF, $H_2SO_4$, $H_3PO_4$ and their mixtures.

16. The process according to claim 13, wherein the metal is aluminum and the Broensted acid is HCl.

17. The process according to claim 13, wherein the used acidic ionic liquid catalyst has been used to catalyze a Friedel-Craft reaction.

18. The process according to claim 17, wherein the Friedel-Craft reaction is alkylation.

19. The process according to claim 13, wherein the conditions include contacting the used acidic ionic liquid catalyst with sufficient amounts of metal and excess acid to generate sufficient hydrogen gas at temperatures of −20° C.-200° C., pressures of atmospheric-5000 psig, and in a normal hydrocarbon solvent.

20. The process according to claim 19, wherein the normal hydrocarbon solvent is selected from the group consisting of normal hydrocarbons ranging from $C_5$-$C_{15}$.

21. The process according to claim 13, wherein the used acidic ionic liquid catalyst comprises an imidazolium, a pyridinium, a phosphonium, a tetralkylammonium derivative, or their mixtures.

22. The process according to claim 13, wherein the used acidic ionic liquid catalyst is a chloroaluminate ionic liquid.

23. The process according to claim 21, wherein the used acidic ionic liquid catalyst is a chloroaluminate ionic liquid.

24. The process of claim 1, claim 13, or claim 2, wherein the time is from 0.1 minute to 24 hours.

25. The process of claim 1, or claim 13, wherein the regenerated ionic liquid catalyst is active for paraffin alkylation.

* * * * *